United States Patent [19]

Garnys

[11] 4,111,553
[45] Sep. 5, 1978

[54] MULTI-SAMPLE TRANSPORTING AND HEATING APPARATUS FOR USE IN ATOMIC ABSORPTION SPECTROMETRY

[75] Inventor: Vytenis Peter Garnys, Bondi, Australia

[73] Assignee: Unisearch Limited, Australia

[21] Appl. No.: 775,289

[22] Filed: Mar. 7, 1977

[30] Foreign Application Priority Data

Mar. 30, 1976 [AU] Australia .............................. PC5415

[51] Int. Cl.² .............................................. G01N 1/00
[52] U.S. Cl. ....................................... 356/36; 356/85; 356/244
[58] Field of Search ...................... 356/36, 38, 85-87, 356/244

[56] References Cited

U.S. PATENT DOCUMENTS

| | | | |
|---|---|---|---|
| 3,174,393 | 3/1965 | Dewey et al. | 356/86 |
| 3,419,359 | 12/1968 | Anderson et al. | 356/87 UX |
| 3,832,060 | 8/1974 | Dahlquist | 356/85 X |
| 4,008,963 | 2/1977 | Huber et al. | 356/85 |

OTHER PUBLICATIONS

*Advances in Automated Analysis, Technicon International Congress,* 1969, vol. II, Mediad, Inc., NY, 1970 pp. 315-320.

*Primary Examiner*—F. L. Evans
*Attorney, Agent, or Firm*—Browdy and Neimark

[57] ABSTRACT

Samples to be analyzed by atomic absorption spectrometry, are introduced into an electrothermally heated furnace for sample atomization by means of a filament arranged to be passed longitudinally through the furnace and to be heated by an electrically heated current. A plurality of liquid samples are deposited at regular intervals along the length of the filament which is then heated to simultaneously dry and ash the samples and is thereafter advanced through the furnace sample by sample to enable rapid sequential analysis to be carried out in this furnace. Preferably the filament is provided along its length with means such as short coils of filament material that act to hold the liquid samples.

6 Claims, 2 Drawing Figures

MULTI-SAMPLE TRANSPORTING AND HEATING APPARATUS FOR USE IN ATOMIC ABSORPTION SPECTROMETRY

This invention relates to apparatus used in conjunction atomic absorption spectrometers using electrothermally heated furnaces for sample atomization, similar in operation to the instruments described by Kirkbright G. F. in The Analyst, 96,609 (1971) said to have applications for the chemical analysis of a wide range of the elements. Spectrometers of this kind described previously effected analysis of liquids by thermal atomization of single samples of the liquid which were dried within the furnace.

The fact that known spectrometers are capable of dealing only with single samples at a time necessarily extends the time needed for treating numbers of samples. The object of the present invention is to provide an arrangement allowing rapid sequential multi-sample analysis.

The present invention thus consists in an atomic absorption spectrometer using an electro-thermally heated furnace for sample atomization having associated with the furnace a filament arranged to be passed longitudinally through the furnace and to be heated by the passage of an electric current therethrough, the filament being adapted to receive a plurality of liquid samples deposited at regular intervals along its length, means being provided to pass an electric current through said filament to simultaneously dry and ash said samples and means being provided to advance the filament sample by sample through the furnace to enable rapid sequential analysis of the samples to be carried out therein.

In order that the nature of the invention may be better understood a preferred form thereof is hereinafter described by way of example with reference to the accompanying drawings, in which.

Figure 1:
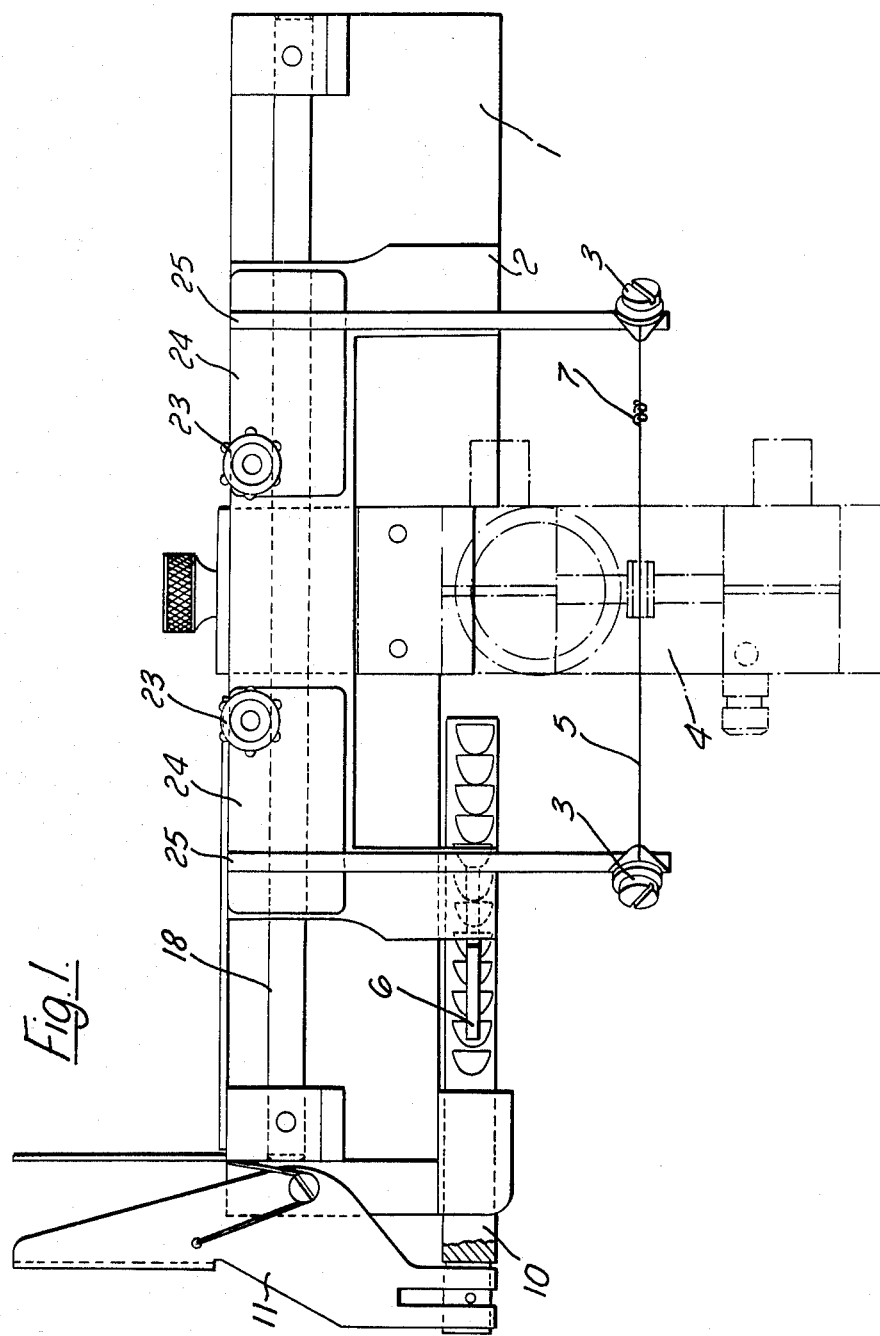
FIG. 1 is a plan view of apparatus according to the present invention.
Figure 2:
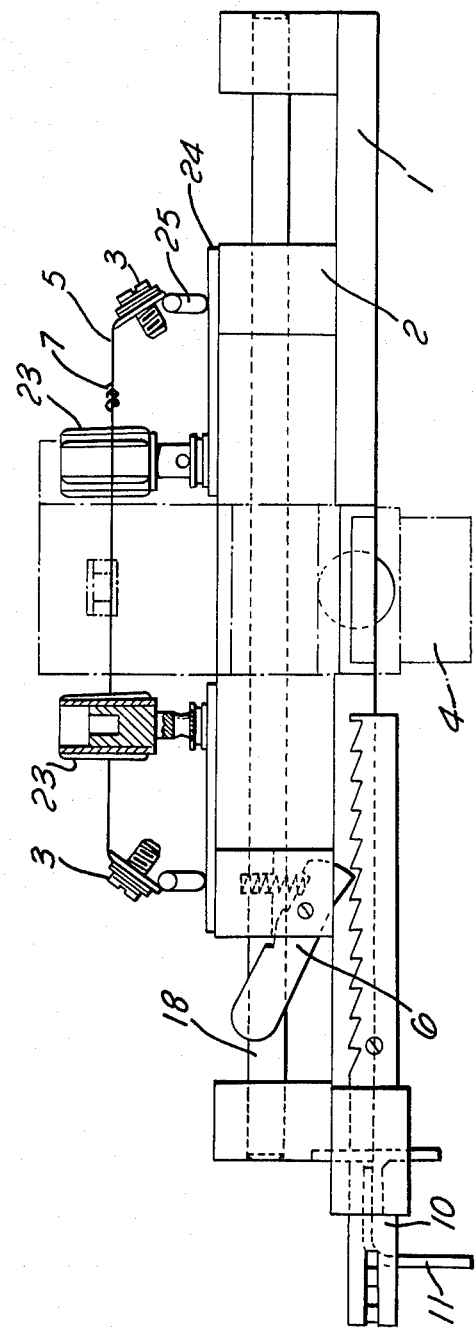
FIG. 2 is an elevation of the apparatus shown in FIG. 1.

In the drawings a commercially available carbon tube furnace body is shown in outline at 4, the outline being indicated by a broken line. As this does not form a part of the present invention it will not be described in detail. To the furnace body 4 is attached a base plate 1 on which is mounted an insulated assembly carriage 2 which is guided for lateral movement on the base plate 1 by the slide rod 18. On the insulated assembly carriage 2 are mounted a pair of filament support rod conducting plates 24 on which are filament power supply terminals 23 and filament support rods 25. At the end of each filament support rod 25 is a filament anchorage screw 3, the filament 5 extending between the filament anchorage screws 3. The filament, which consists preferably of a tungsten wire or a strip of graphite, tantalum or other suitable material, may be heated by the application of a d.c. or a.c. voltage to the terminals 23.

Movement of the insulated assembly carriage in relation to the base plate 1 is effected by means of the pivoted lever 11 the rod 10 and the ratchet transport mechanism 6. In use, the carriage 2 is set at one end of its travel so that one end of the filament 5 lies within the furnace. A series of liquid samples are then deposited at regular intervals along the filament.

The samples are preferably constrained within a limited length of the filament by constraining means consisting, for example, of short lengths of filament wound, as a coil spring, about the supporting filament 5 or by small depressions in a filament strip or by constructing the filament as a chain or a series of linked cups. One short length of filament 7 wound as a spring is shown, by way of example, in the drawings. In practice, a series of these is arranged along the length of the wire 5 at appropriate intervals.

A low voltage is then applied across the terminals 23 and this is gradually increased to heat the filament and thereby dry, and subsequently ash, the samples deposited on it. The transport mechanism is then used to transport the filament sample by sample through the furnace. This is done by moving the end of the lever 11 to the right as seen in FIG. 1; this transports the carriage 2 one step to the left by means of the ratchet mechanism 6 which corresponds to the distance between samples on the wire 5. The action is repeated until all samples have been transported through the furnace. The atomic absorption signal for each sample in turn is recorded in the conventional manner.

The form of apparatus described above is given only by way of example and as will be readily appreciated by those skilled in the art the principles of the invention may be embodied in a wide variety of different forms of apparatus and in particular the transport system used for moving the filament through the furnace may be constructed so as to operate automatically to feed the samples through the furnace after they have been dried and ashed. Also the geometry of the filament may be varied so as to pass, as a ring or loop, continuously through the furnace or, with furnaces having different electrode arrangements, the filament may pass through the furnace walls, at 90° or other angles to the light beam used in such furnaces for sample analysis.

While there have been previous proposals for "flameless" Atomic Absorption Spectrometers these all have the defect that a plurality of samples cannot be dried and ashed simultaneously and thereafter fed to a furnace for sequential atomization.

Advantages flow from the apparatus described in that, when a current is passed through the filament during heating of the furnace, the increasing electrical resistance of the filament with increasing temperature from the furnace enables the atomization of the sample to be carried out at lower furnace temperatures and with lower furnace current consumption than if the furnace alone was heating the sample.

Further advantages arise from the fact that pre-atomizing the sample may be effected by passing such a current through the filament as to heat the filament at a faster, similar or slower rate than the furnace. Furthermore, the sample aliquots are located within a smaller volume than in some known forms of apparatus thus improving accuracy and reliability. The main advantage of the invention however lies in the more rapid sample processing that may be carried out.

I claim:

1. Sequential multi-sample analysis transporting and heating apparatus for use with an atomic absorption spectrometer using an electrothermally heated furnace for sample atomization, comprising a filament arranged to be passed longitudinally through the furnace and to be heated by the passage of an electric current therethrough, the filament being adapted to receive a plurality of liquid samples deposited at regular intervals along its length, heating means for passing an electric current through said filament to simultaneously dry and ash the samples, and advancing means for advancing said filament, sample by sample, through the furnace to enable rapid sequential analysis of the samples to be carried out therein.

2. An apparatus as claimed in claim 1, further including a base plate attachable to the furnace body of the spectrometer, an insulated carriage slidably mounted on said base plate, and electrically conductive supporting means for carrying said filament, mounted on said insulated carriage, and wherein said advancing means comprises transport means on said base plate for guiding the movement of said carriage and thereby effecting transport of said filament through the furnace, sample by sample.

3. An apparatus as claimed in claim 1 further including constraining means, connected to said filament, for constraining each sample within a limited length of the filament.

4. An apparatus as claimed in claim 3 wherein each said constraining means consists of a short length of filament wound in the manner of a coil spring about said filament.

5. An apparatus as claimed in claim 2 further including constraining means, connected to said filament, for constraining each sample within a limited length of the filament.

6. An apparatus as claimed in claim 5 wherein each said constraining means consists of a short length of filament wound in the manner of a coil spring about said filament.

* * * * *